US00PP16505P2

(12) United States Plant Patent
Lim

(10) Patent No.: US PP16,505 P2
(45) Date of Patent: May 2, 2006

(54) SHRUB ROSE PLANT NAMED 'BAINGO'

(50) Latin Name: *Rosa hybrida*
Varietal Denomination: BAIngo

(75) Inventor: Peter P. Lim, Yamhill, OR (US)

(73) Assignee: Bailey Nurseries, Inc., St. Paul, MN (US)

( * ) Notice: Subject to any disclaimer, the term of this patent is extended or adjusted under 35 U.S.C. 154(b) by 54 days.

(21) Appl. No.: 10/991,362

(22) Filed: Nov. 19, 2004

(51) Int. Cl.
*A01H 5/00* (2006.01)

(52) U.S. Cl. ..... Plt./108

(58) Field of Classification Search ..... Plt./108, Plt./149, 150
See application file for complete search history.

*Primary Examiner*—Anne Marie Grunberg
*Assistant Examiner*—June Hwu
(74) *Attorney, Agent, or Firm*—Buchanan Ingersoll PC

(57) ABSTRACT

A new and distinct variety of landscape shrub rose plant is provided which abundantly forms on a substantially continuous basis in clusters attractive double intense medium red blossoms with ruffled petals that fade with a hint of bright red-purple. The blossoms also display a light spice fragrance. The plant exhibits a dense upright and bushy growth habit, attractive semi-glossy medium green foliage, and good tolerance to Black Spot and Powdery Mildew. The attractive medium green semi-glossy foliage contrasts nicely with the bold ruffled medium red blossom coloration. The new variety is particularly well suited for growing as attractive ornamentation in parks and gardens.

2 Drawing Sheets

Botanical commercial classification: *Rosa hybrida*/Shrub Rose Plant.
Varietal denomination: cv. BAIngo.

SUMMARY OF THE INVENTION

The new variety of *Rosa hybrida* landscape shrub rose plant was created at Yamhill, Oreg., U.S.A., during 1996 by artificial pollination wherein two parents were crossed which previously has been studied in the hope that they would contribute the desired characteristics. The female parent (i.e., the seed parent) was the 'POUlurt' varietal U.S. Plant Pat. No. 9,637). The 'POUlurt' variety sometimes is known as the 'Aspen' variety. The male parent (i.e., the pollen parent) was the hybrid tea 'BAIlgance' variety (non-patented in the United States). The parentage of the new variety can be summarized as follows:

'POUlurt'×'BAIlgance'.

The seeds resulting from the above pollination were sown and plants were obtained which were physically and biologically different from each other. Selective study resulted in the identification during 1998 of a single plant of the new variety having the distinctive ornamental characteristics hereafter described.

It was found that the new variety of the present invention:

(a) exhibits a dense upright and bushy growth habit, (b) forms on a substantially continuous basis in clusters attractive double intense medium red blossoms with ruffled petals that fade with a hint of bright red-purple, (c) forms attractive semi-glossy medium green foliage, (d) is highly tolerant to Black Spot and Powdery Mildew; and (e) is particularly well suited for growing as attractive ornamentation in parks and gardens.

The young red buds open to bold bright medium red blossoms that are blended with dark pink. The blooms bear clear red with ruffled edges that tend to hide the center. Excellent repeat blooming is provided with the flowers commonly being substantially evenly distributed over the plant. As the blooms fade more pink commonly is displayed as well as a hint of bright red-purple.

The new variety well meets the needs of the horticultural industry and can be grown to advantage in the landscape where attractive ornamentation is desired. The intense medium red blossoms contrast nicely with the semi-glossy medium green foliage. An attractive new shrub rose that can be grown in U.S.D.A. Hardiness Zone Nos. 4 to 9 is provided.

The new variety can be readily distinguished from other varieties including its ancestors. For instance, the 'POUlurt' variety forms medium yellow blossoms having approximately 15 to 25 petals, and the 'BAIlgance' variety which is a Hybrid Tea forms dark red very double blossoms having a diameter of approximately 11 cm with approximately 34 to 40 petals that are borne singly, and forms large glossy dark green foliage.

The new variety also can be readily distinguished from the 'BAIhero' (U.S. Plant Pat. No. 15,400, granted Dec. 7, 2004) and 'Champlain' (non-patented in the United States) varieties. More specifically, the 'BAIhero' variety forms larger blossoms and lighter green foliage, and the 'Champlain' variety is a hybrid Kordesii that forms dark red blossoms.

The new variety beginning in August 1997 has been found to undergo asexual propagation by budding on an understock and by the rooting of cuttings. 'Dr. Huey' rootstock was used during the budding. Such asexual propagation by these techniques at Yamhill, Oreg., U.S.A., St. Paul, Minn., U.S.A., and at Phoenix, Ariz., U.S.A. has shown that the characteristics of the new variety are stable and are strictly transmissible by such asexual propagation from one generation to another. Accordingly, the new variety reproduces true to type. The new variety grows well on its own roots.

Initially the new plant was designated 96T420 and subsequently was designated 03R507 during further evaluations. The new plant has been named the 'BAIngo' variety, and currently is being marketed while using the GARDEN ART and LAST TANGO trademarks.

BRIEF DESCRIPTION OF THE PHOTOGRAPHS

The accompanying photographs show as nearly true as it is reasonably possible to make the same in color illustrations of this character, typical specimens of the new variety. The rose plants of the new variety had been propagated by the rooting of cuttings, were approximately two and three years of age, and were being grown outdoors during the 2003 and 2004 seasons at St. Paul, Minn., U.S.A., and at Yamhill, Oreg., U.S.A.

DETAILED DESCRIPTION

Figure 1:
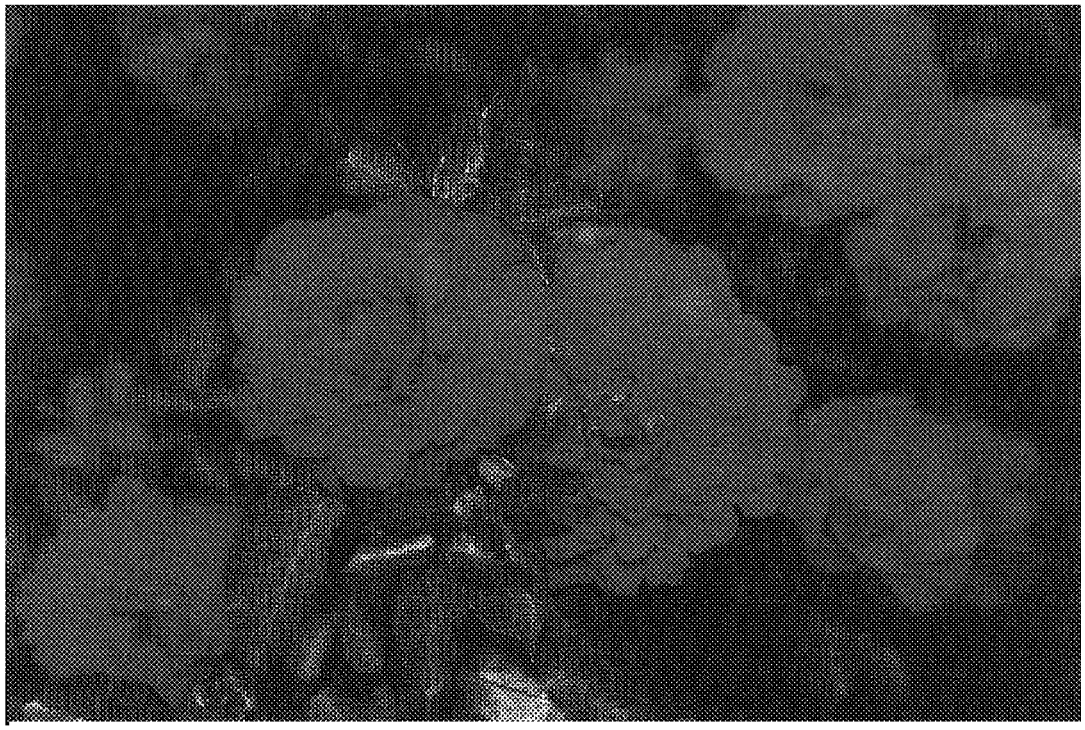
FIG. 1 illustrates typical clusters of intense medium red blossoms and foliage of the new variety.
Figure 2:
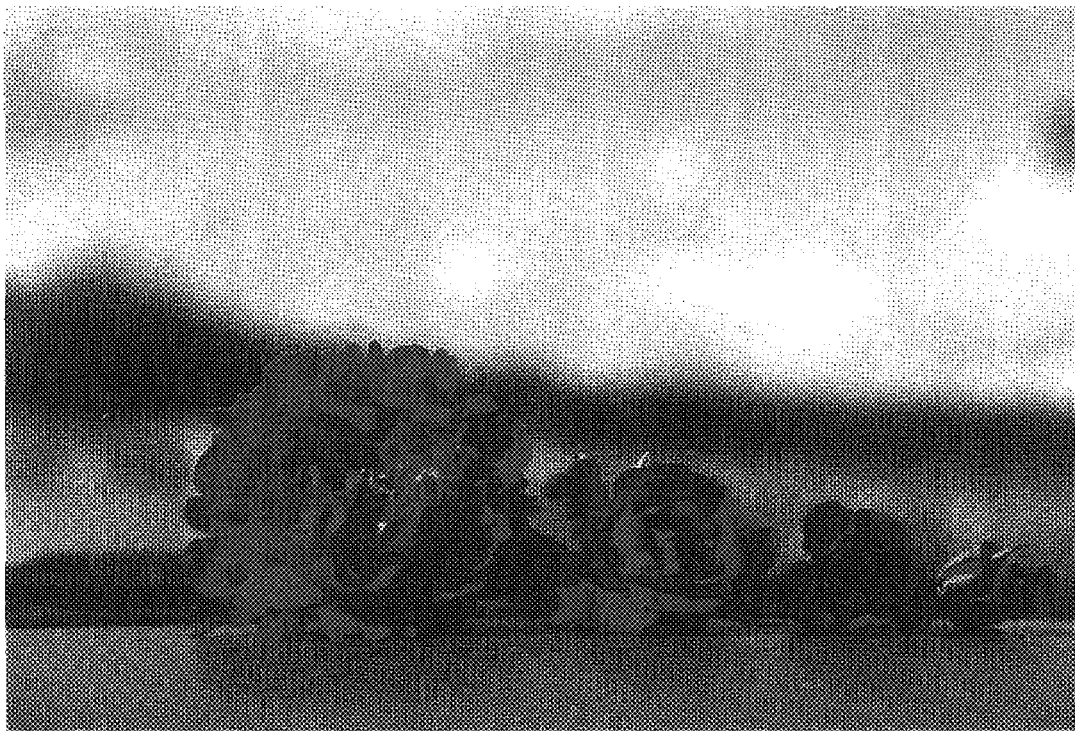
FIG. 2 illustrates typical blossoms in progressive stages of opening.
Figure 3:
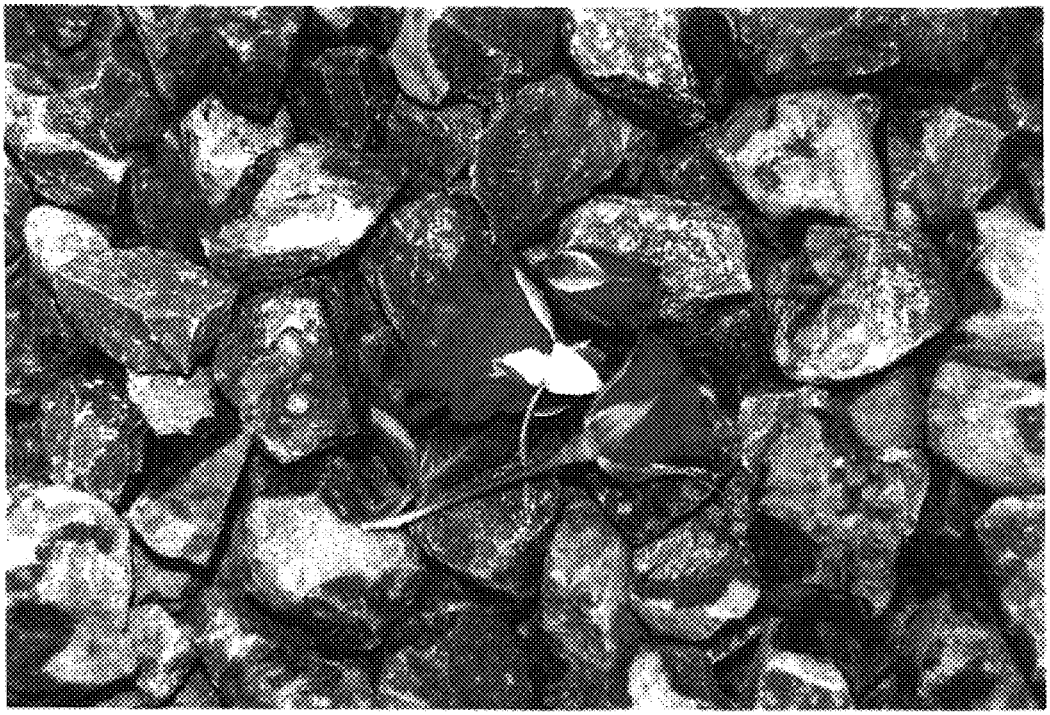
FIG. 3 illustrates typical blossoms in the early stages of opening wherein the sepals also are visible.
Figure 4:
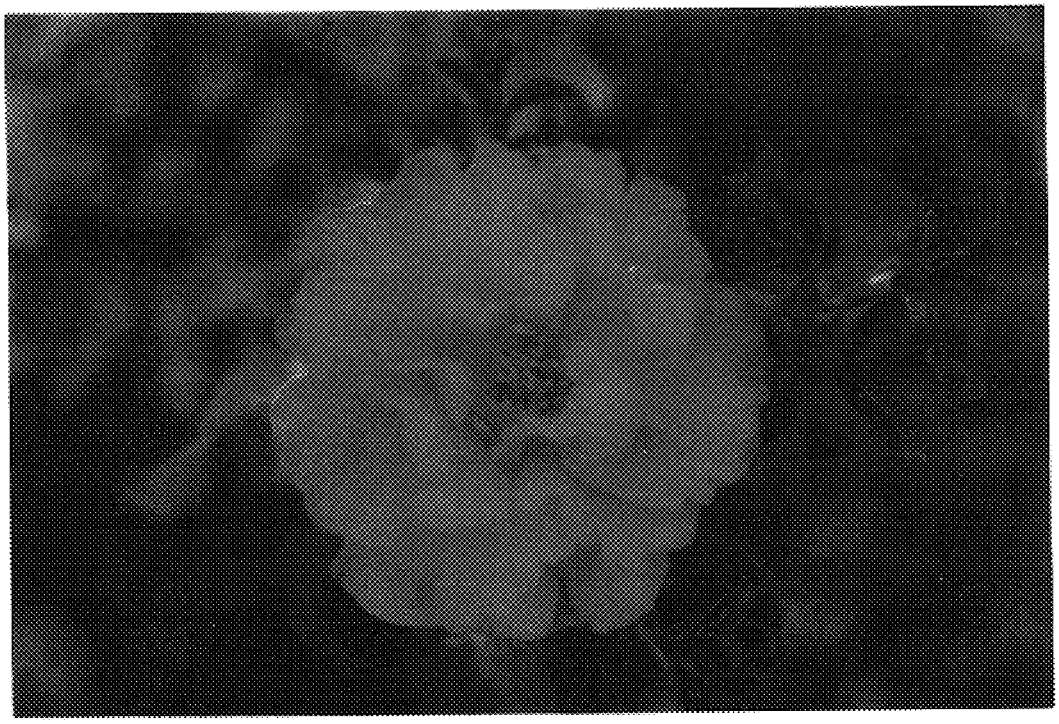
FIG. 4 illustrates a typical fully open blossom wherein the ruffled petals are shown as well as the onset of a hint of red-purple coloration.

The chart used in the identification of the colors is that of The Royal Horticultural Society (R.H.S. Colour Chart). Common color terms are to be accorded their ordinary dictionary significance. The description is based on the observation of two, three and four year-old plants while grown outdoors on their own roots during June 2003, at Yamhill Oreg., U.S.A. and during July 2004 at St. Paul, Minn., U.S.A.

Botanical classification: *Rosa hybrida* 'BAIngo'.
Class: Landscape Shrub.
Plant:
- *Height*.—Approximately 50 cm to 1.25 m at the end of the growing season. The height is influenced by the length of the growing season.
- *Width*.—Approximately 40 cm to 1.0 m on average at the end of the growing season. The width is influenced by the length of the growing season.
- *Habit*.—Dense, upright and bushy.

Branches;
- *Color*.—Young stems: Yellow-Green Group 146B suffused with Greyed-Purple Group 187A and 187B. Adult wood: Yellow-Green Group 147B with streaks of Grey-Brown Group 199B.
- *Texture*.—Young stems are glabrous and adult wood is mostly glabrous with bark-like ridges.
- *Thorns*.—Size: approximately 0.3 cm. in length on average. Color: Red-Purple Group 59B and 59C. Shape: generally triangular to slightly hooked. Quantity: approximately 6 on average over a length of 5 cm.

Leaves:
- *Stipules*.—Generally parallel with the auricle facing outward, approximately 1.4 cm in length on average, approximately 4.7 mm in width on average, the shape tends to be variable ranging to semi-circular at the middle with narrowing at the apex to straight, the color of the upper surface is commonly Greyed-Red Group 181B on the central ridge and outer wings and Yellow-Green Group 144A and 144B on ridges on either side of central ridge, and the color of the under surface is Yellow-Green Group 144B.
- *Petioles*.—Upper surface: Yellow-Green Group 146A. Under surface: Yellow-Green Group 146B and 146C. Length: approximately 1.9 cm on average. Texture: generally glabrous and tomentose on the upper side to varying degrees.
- *Size*.—Length: commonly appropriately 9.0 cm on average. Width: commonly approximately 6.9 cm on average.
- *Leaflets*.—Number: 3, 5 (most often), and 7. Shape: generally elliptical with a rounded base and an acuminate tip. Margin: serrulate. Texture: bears a semi-glossy finish. Length: approximately 3.4 cm on average. Width: approximately 2.2 cm on average. General appearance: medium green with a semi-glossy surface when mature. Color (young foliage): Upper surface: Yellow-Green Group 146B with highlights of Greyed-Purple Group 187C. Under surface: Greyed-Purple Group 187C with highlights of Yellow-Green Group 144B. Color (adult foliage): Upper surface: Yellow-Green Group 147A. Under surface: Yellow-Green Group 148B.

Inflorescence:
- *Number of flowers*.—Commonly approximately 3 blooms in a cluster on average per lateral stem.
- *Peduncel*.—Between Yellow-Green Group 144A and 144B with highlights of Greyed-Purple Group 185A, moderate to strong in strength, glabrous with a few short spines, and commonly approximately 2.5 cm in length.
- *Sepals*.—Upper surface: commonly near Yellow-Green Group 145B. Under surface: Green Group 143B and 143C with highlight of Greyed-Purple Group 185A and 185B. Size: approximately 2.5 cm in length. Shape: sharply pointed tip and truncate base, upright in the bud stage, generally horizontal when opening, and reflexed at full bloom. Texture: tomentose on the upper surface and strigose with short hairs on the under surface. Foliaceous appendages: commonly present on the two outer sepals with one appendage per sepal, approximately 6 mm in length on average with an entire to serrate margin.
- *Buds*.—Shape: slender ovoid. Size: medium. Length: approximately 2.8 cm on average. Diameter: approximately 2.15 cm on average. Color: Upper petal surface: between Red Group 46A and 46B. Under petal surface: Red Group 53A. Basal petal spot: Yellow Group 13B.
- *Flower*.—Arrangement: in a cluster or cyme. Diameter: approximately 7.25 cm on average. Form: double. Color: (when opening begins): Upper surface: Red Group 46B. Under surface: Red Group 53C. Color (when blooming): Upper surface: Red Group 45B and 45C. Under surface: Red Group 53C. Color (at end of blooming): Upper surface: Red Group 46C blended with Red Group 54A. Under surface: Red Group 53C blended with Red Group 52A. Color (basal petal spot): Yellow Group 4A. Fragrance: light spice. Lasting quality: the blossoms commonly last approximately 5 to 7 days on average depending upon the temperature and sunlight exposure. Petal number: commonly approximately 25 on average under normal growing conditions. Petal shape: wedge-shaped commonly with a curled apex and a ruffled edge when fully open. Petal size:

approximately 4.0 cm on average. Petal texture: glabrous, smooth, and satiny. Petal drop: commonly the petals detach cleanly at full blossom maturity. Anther size: approximately 1.3 mm in length on average, and approximately 0.8 mm in width on average. Anther color: Greyed-Yellow Group 162A. Pollen color: Yellow Group 13A. Filament number: commonly approximately 45 on average. Filament length: approximately 7.3 mm on average. Filament color: Yellow Group 3B. Pistils: Approximately 26 on average, and are separate and free. Stigma color: Yellow Group 11A. Stigma size: approximately 1.1 mm in length on average, and approximately 0.7 mm in diameter on average. Style color: Red Group 43A. Style length: approximately 5.0 mm on average. Receptacle: urn-shaped when the flower is fully open, approximately 8.0 mm in length on average, approximately 6.9 mm in diameter on average, Yellow-Green Group 146B and 146C in coloration with some coloration of Greyed-Purple Group 184A on the side exposed to the sun, generally glabrous with some glaucous covering of Yellow-Green Group 144A to 144C in coloration with some coloration of Greyed-Purple Group 184B on the side exposed to the sun. Hips: elongated-obovate in configuration, glabrous with some ridges, approximately 1 cm in length, approximately 8 mm in width, and Greyed-Red Group 176A suffused with Yellow-Green Group 147B in coloration. Seeds: dark beige in coloration and approximately 4 mm in length.

Development:

*Vegetation*.—Vigorous, compact and dense.

*Blooming*.—Substantially continuous, everblooming.

*Resistance to diseases*.—Highly tolerant to Black Spot, and Powdery Mildew.

*Hardiness Zone*.—U.S.D.A. Hardiness Zone Nos. 4 to 9.

What is claimed is:

1. A new and distinct variety of landscape shrub rose plant characterized by the following combination of characteristics:

(a) exhibits an upright and bushy growth habit, (b) forms on a substantially continuous basis in clusters attractive double intense medium red blossoms with ruffled petals that fade with a hint of bright red-purple.

(c) forms attractive semi-glossy medium green foliage, (d) is highly tolerant to Black Spot and Powdery Mildew, and (e) is particularly well suited for growing as attractive ornamentation in parks and gardens;

substantially as herein shown and described.

* * * * *